US006534318B2

(12) United States Patent
Roussis et al.

(10) Patent No.: US 6,534,318 B2
(45) Date of Patent: Mar. 18, 2003

(54) MASS SPECTROMETRIC MULTIVARIATE ANALYSIS

(75) Inventors: Stilianos George Roussis, Brights Grove (CA); Barbara Joanne Shannon, Sarnia (CA); Biddanda Umesh Achia, Swedesboro, NJ (US); Olga Puzic, Sarnia (CA)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/021,960

(22) Filed: Dec. 13, 2001

(65) Prior Publication Data

US 2002/0151083 A1 Oct. 17, 2002

Related U.S. Application Data

(60) Provisional application No. 60/258,900, filed on Dec. 15, 2000, provisional application No. 60/256,129, filed on Dec. 15, 2000, and provisional application No. 60/258,899, filed on Dec. 15, 2000.

(51) Int. Cl.[7] .............................................. G01N 33/00
(52) U.S. Cl. ........................ 436/139; 436/173; 436/25; 436/29; 436/30
(58) Field of Search ................................ 436/139, 173, 436/25, 29, 30

(56) References Cited

PUBLICATIONS

Hein et al. "Reverse search and related processing of gas chromatographic/mass spectrometric data from petroporphyrin analyses", Anal. Chem., 1985, v. 57 (9), pp. 1872–1879.*

Rullkoetter et al. "Dead Sea asphalt in Egyptian mummies: molecular evidence", Naturwissenschaften (1988), 75(12), 618–21.*

Eckardt et al. "Multimolecular data processing and display in organic geochemistry: the evaluation of petroporphyrin GC–MS data", Org. Geochem., 1988, 13(4–6), 673–82.*

Roques et al. "Using gas chromatography/mass spectroscopy fingerprint analyses to document process and progress of oil degradation", J. Environ. Qual., 194, 23)4), 851–5.*

Gale et al. "A chemical characterization of asphalt using thermal chromatography with mass spectrometry", Fuel Sci. Technol. Int. (1992), 10(4–6), 1059–69, Abstract.*

Gawel e al. "Study of saturated components in asphalts", Petroleum Science and Technology (1997), 15(7 & 8).*

Ramadhan et al. "A Study of aromatic hydrocarbons in Qaiyarah naphtha fraction 50–165 oC using gas chromatography/mass spectroscopy", Petroleum Science and Technology (1997), 15(1 & 2), 127–135.*

Hunt, J. E. "Characterization of coal–derived materials by laser desorption mass spectrometry", Prepr. Paper.–Am. Chem. Soc., Div. Fuel Chem., 1991, v. 36, N. 3, pp. 1325–1329 Abstract.

Rullkoetter, J. "Dead Sea asphalt in Egyptian mummies: molecular evidence", Naturwissenschaften, 1988, v. 75, N. 12, pp. 618–621, Abstract.

Sturm, G. P. "Composition of liquids from coals of different rank", Report (1980), DOE/BETC/RI–80/1, 48 pp. Energy Res. Abstr. 1980, 5(22), Abstr. No. 34496, Abstract.

Gale, P. "A chemical characterization of asphalt using thermal chromatography with mass spectrometry", Fuel Sci. Technol. Int., 1992, v. 10, NN. 4–6, pp. 1059–1069, Abstract.

Hayes, M. H. B. "Bitumen. 2. Changes in bitumen during weathering", Fuel, 1972, v. 51, N. 1, pp. 32–37, Abstract.

* cited by examiner

Primary Examiner—Jill Warden
Assistant Examiner—Yelena Gakh
(74) Attorney, Agent, or Firm—Charles J. Brumlik

(57) ABSTRACT

This invention relates to the selection of a crude oil or crude oil blend for the production of high-performing paving asphalt based on molecular composition of the asphalt and of the parent crude oil or crude oil blend based, at least in part, on high resolution mass spectrometric measurements and relationships to rheological properties.

13 Claims, 4 Drawing Sheets

| Crudes | Hydrocarbon Moment Calculations | | | |
|---|---|---|---|---|
| | Hi | Hz | Hc | Hm |
| MEN 79 | 211.71 | 22.59 | 15.47 | 475.91 |
| BCF-22 94 | 245.35 | 25.37 | 18.29 | 514.53 |
| BCF-22 156 | 256.10 | 24.72 | 17.14 | 499.29 |
| BCF-22 404 | 233.30 | 23.67 | 16.01 | 484.19 |
| CL 382 | 169.17 | 20.56 | 15.72 | 478.74 |
| CL 86 | 189.05 | 22.28 | 16.74 | 493.18 |
| CL 216 | 196.54 | 21.96 | 15.72 | 480.34 |
| BR 91 | 281.16 | 26.93 | 16.06 | 484.81 |
| AHF 66 | 222.29 | 26.36 | 14.23 | 460.68 |
| AHF 166 | 251.21 | 24.87 | 16.68 | 492.19 |

MASS SPECTROMETRIC MULTIVARIATE ANALYSIS

This Application claims priority from Provisional Patent Application U.S. Serial Nos. 60/258,900; 60/256,129; and 60/258,899, all filed Dec. 15, 2000.

BACKGROUND

Multivariate models are the basis by which on-line infrared analyzers are used to estimate component concentrations such as benzene content, saturates content, aromatics content and olefin content for motor gasolines, diesel fuels, jet fuels and process streams, and properties such as research and motor octane number of gasolines and cetane number for diesel fuels from infrared spectra. For example, Maggard describes the use of multivariate models for measuring paraffin, isoparaffin, aromatics, naphthene and olefin contents of motor gasolines and gasoline components (U.S. Pat. No. 5,349,189). Maggard also describes the use of MLR for measuring octane and cetane numbers (U.S. Pat. Nos. 4,963, 745 and 5,349,188). Perry and Brown (U.S. Pat. No. 5,817, 517) describe the use of FT-IR for determining the composition of feeds to hydrocarbon conversion, separation and blending processes.

The use of multivariate models is not limited to infrared analyzers. Jaffe describes the use of gas chromatography to estimate octane numbers for gasolines (U.S. Pat. No. 4,251, 870). Ashe, Roussis, Fedora, Felsky and Fitzgerald describe the use of gas chromatography/mass spectrometry (GC/MS) and multivariate modeling for predicting chemical or physical properties of crude oils (U.S. Pat. No. 5,699,269). Cooper, Bledsoe, Wise, Sumner and Welch describe the use of Raman spectroscopy and multivariate modeling to estimate octane numbers and Reid vapor pressures of gasolines (U.S. Pat. No. 5,892,228).

Conventional asphalt binder specifications address binder properties such as penetration, viscosity, ductility, softening point, etc. which have a history of empirical correlation with asphalt pavement performance in service. The failure of specifications based on conventional properties to provide stable and durable road surfaces has resulted in the development of SUPERPAVE™ specifications for rheologically-simple asphalt binders, based on rheological performance under limited frequency and temperature conditions. The SUPERPAVE™ specifications do not currently deal with rheologically-complex materials and do not currently differentiate performance of asphalts in the same performance grade (PG).

Attempts to rank molecular components and identify an "ideal" asphalt composition based on conventional and SUPERPAVE™ performance parameters have not been successful. The relationship between composition and performance is masked by the use of a single performance parameter to rank the performance of each asphalt or vacuum residuum. The assigned ranking varies widely depending on which parameter is chosen (i.e., pen@25, SUPERPAVE spread between PG temperatures Tmax and T min, G* @Tg, etc.). The assigned ranking is also found to be too sensitive to the distillation cut temperature of the residuum.

It would be beneficial to find a method to rank and identify acceptable or ideal asphalt compositions by testing the feedstock or blends under consideration prior to asphalt production.

SUMMARY

The present invention uses a combination of conventional and rheological parameters to develop a composite rheological ranking which accurately predicts the relative field performance of the asphalts and that rheologically-similar asphalts and vacuum residua exhibit commonalties in molecular composition, preferably measured by high resolution mass spectrometry. The abundance of specific molecular structures is indicative of superior asphalt pavement performance.

DETAILED DESCRIPTION

A method has been developed to rapidly predict and to modify asphalt quality of an unknown crude oil. A definitive relationship between molecular composition and asphalt pavement performance is required in order to achieve that goal. The relationship between crude slate and molecular composition of asphalt, independent of penetration or performance grade, was established using high-resolution mass spectroscopy (HR/MS). Approximately 120 molecular groups were identified having the molecular structure $[C_nH_{(2n\pm z)}\text{—R}]$ where n was generally greater than ten; z ranged from zero to approximately 44; and R is a heteroatom or heteroatom combination containing sulfur, nitrogen, or oxygen. The molecular groups are used to distinguish between asphalts from different crude slates, and are relatively insensitive to distillation cut temperatures of residua from the same crude slate. The link between asphalt composition and pavement performance is established through empirical (specification) or mechanistic (rheological) measurements on asphalt binders in the laboratory.

The present invention is a method to determine the suitability of crude oils, mixtures of different crude oils (crude slate) and crude oil fractions as feed for asphalt production based on the chemical concentration of one or more of a number of molecular fragments in HR/MS of a feed sample. A specific fingerprint range will include individual molecular components which are expected to perform adequately in asphalt.

Determination of optimal asphalt composition from molecular moments is preferably accomplished by the process:

a) select the asphalt or residuum, b) perform conventional, SUPERPAVE™, and/or Theological tests, c) determine the rheological index of the sample, d) determine the mean Theological index of the crude slate (RI'), e) assign the Theological group (RG, e.g., Groups I–IV), f) calculate mean intensity, aromaticity, carbon number, and molecular weight for each RG, g) plot mean values of Z=f(I), I=f(Z), MW=f(Z), C#=f(Z) for each molecular group (hydrocarbon, sulfur, oxygen, etc.), h) calculate molecular moments as=SUM(intensity× aromaticity)/SUM(aromaticity)

i) compare the molecular profiles of good (Group I) and poor (Group IV) asphalts, and j) confirm the statistical significance of the differences using molecular moments.

Prediction of asphalt performance from molecular composition is preferably accomplished by the process:

a) select the asphalt or residuum, b) perform high resolution mass spectrometry, c) calculate mean values of Z=f(I), I=f(Z), MW=f(Z), C#=f(Z) for each molecular group d) determine the predicted rheological index of the sample (RI) using the RI=f(moments) equation, e) compare the predicted RI to the RI of good (Group I) and poor (Group IV) asphalts, f) determine the rheological group of the sample, g) predict the suitability of the crude slate for asphalt manufacture based on RG, and h) confirm the suitability of the crude slate for asphalt manufacture by comparing with Group I and Group IV asphalts.

A mathematical description of a preferred model to determine rheological index (RI) in part (d) above is: RI=13.8639−1.18964 E-1*Hc+6.12843 E-2 Hi−4.10153 E-1 Hz−4.68191 E-3 Ni+6.65557 E-3 Oi+5.88057 E-3 Sm−1.42995 E-1 Sz−3.14998 E-3 [C5ARings−]−3.35754 E-3 [C5ARings+] wherein $R^2$=0.95.

Figure 4:
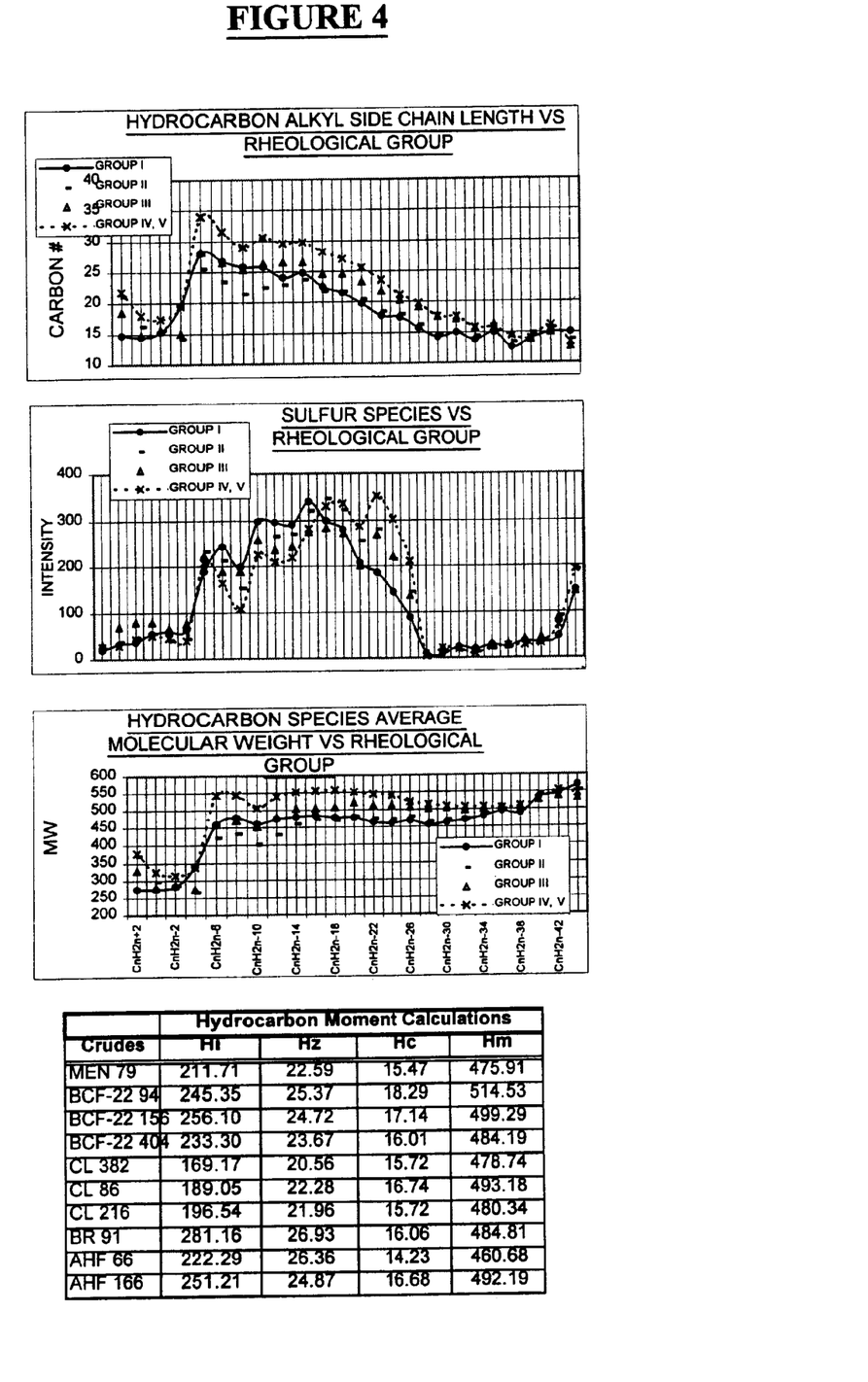
FIG. 4 shows carbon number, molecular weight, and intensity vs. mass for rheological groups (RG) for Groups I–V.

The following molecular moment characteristics for asphalt manufacture are preferred: Paving asphalts that exhibit good performance generally have higher intensity for hydrocarbon molecular groups $10 \leq z \leq 26$, lower intensities for hydrocarbon molecular groups $28 \leq z \leq 44$, higher intensities for sulfur molecular groups $12 \leq z \leq 22$, lower intensities for high-aromaticity sulfur molecular groups $24 \leq z \leq 34$, lower intensity for high-aromaticity $S_2$ molecular groups ($14 \leq x \leq 20$) for $C_nH_{(2n\pm z)}$—R where $R=S_2$, higher intensities for oxygen molecular groups ($12 \leq z \leq 20$) for $C_nH_{(2n\pm z)}$—R where R is a monatomic oxygen substitution and for high-aromaticity oxygen molecular groups ($22 \leq z \leq 32$), and no differences in intensity between the asphalts for molecular groups where z>32. In $C_nH_{(2n\pm z)}=O_2$ molecular groups where $4 \leq z \leq 22$, good and intermediate asphalts exhibit higher intensities than poor asphalts. In $C_nH_{(2n\pm z)}=SO$ good asphalts exhibit higher intensities for $16 \leq z \leq 26$. For $C_nH_{(2n\pm z)}=NO$ good asphalts exhibit higher intensity than poor asphalts for $9 \leq z \leq 21$. Good asphalts exhibit slightly higher intensity for $SO_2$ molecular groups than poor asphalts. FIG. 4 shows these types of comparisons.

Three classes of performance parameters are used in this invention to rank asphalts and vacuum residua and to predict their pavement performance:

I. Conventional parameters which may include properties and specifications such as penetration, viscosity, softening point, ductility, Canadian General Standards Board (CGSB) grade, Fraass point, n-heptane insolubles, elemental analysis etc.

II. SUPERPAVE™ performance parameters which may include Performance Grade (PG XX–YY), SUPERPAVE spread™ (numerical difference between high and low specification temperatures XX and −YY), cross-over temperatures (Tmax, Tmin, and Tfat; the temperatures at which specification stiffness limits are met), and cross-over temperature spread (Tmax−Tmin), etc.

III. Rheological indices from complete rheological analysis within the linear visco-elastic domain of the material.

These may include the SHRP Rheological Model (master curve indices Gg, η0, ωc, and R @ TreF=+10° C.) and Phase Response indices (Tf, Tb, T45 @ δ=10 rad/s isochrone), Black Diagram properties, etc.

Conventional asphalt properties, CGSB grade, SUPERPAVE™ performance parameters and Theological indices all attempt to describe the temperature susceptibility of an asphalt in terms of load-carrying capability, susceptibility to deformation, strain tolerance, and degree of deformation recovery after load removal. Each parameter measures a different aspect of material response. A method of combining the parameters has been developed in this invention to fully describe the behavior of asphalt as a function of crude slate, independent of distillation cut temperature.

Through an iterative process, parameters such as those in Table 1 were selected to rank asphalts and vacuum distillation residua for pavement performance. Because the majority of these parameters are based on classical rheology, they are called rheological performance parameters.

Figure 1:
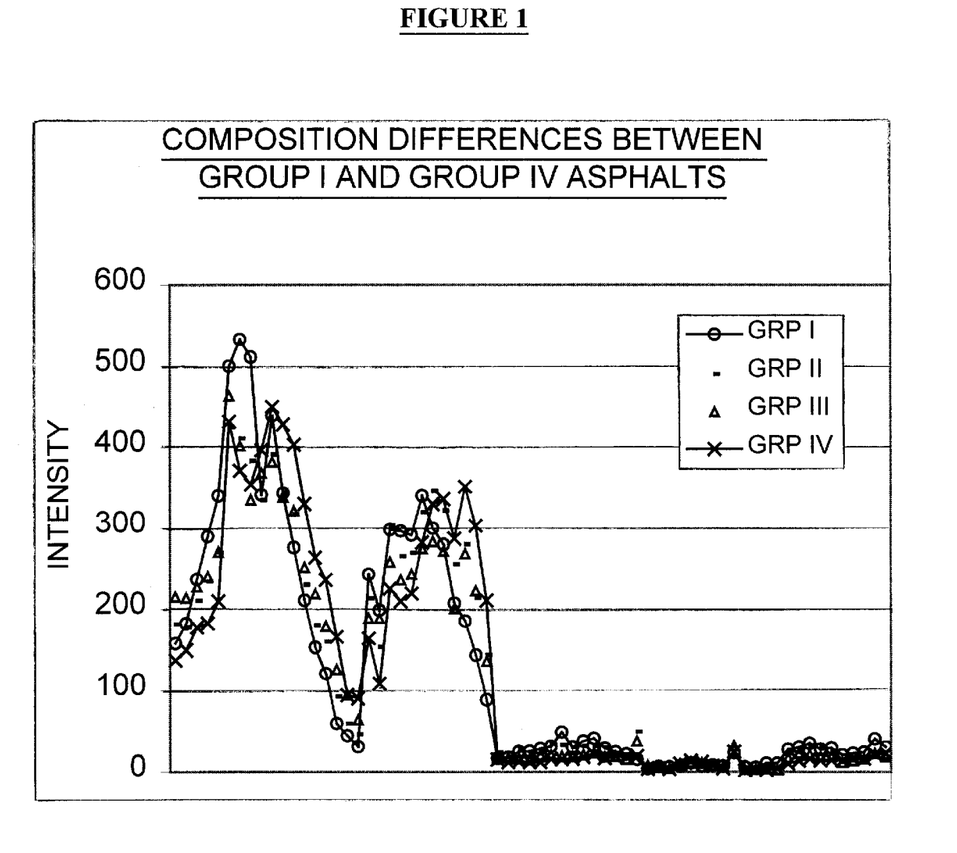
FIG. 1 shows fingerprint spectra (intensity vs. mass) for Group I–IV asphalts.

An ordinal or normalized nominal ranking system is used for parameters such as those in Table 1, based on values which optimize pavement performance in a generalized application. The performance parameters are measured or calculated for each vacuum residuum obtained at a given cut temperature from a given crude oil slate. On a parameter-by-parameter basis, the residua are assigned a ranking for each parameter. Duplicate rankings are permitted when parameters were equivalent or identical. A mean ranking is calculated for the residua based on the ranking of its individual parameters. An overall ranking for each crude slate is determined by calculating the mean of the mean rankings as determined in the previous step for all the residua from the crude slate (FIG. 1). Five paving asphalt rheological "quality" groups are identified based on the Theological rankings where Group I is "excellent" asphalt, Group II is "good" asphalt, Group III is "satisfactory" asphalt, and Groups IV and V are "poor" and "very poor" asphalt.

Figure 3:
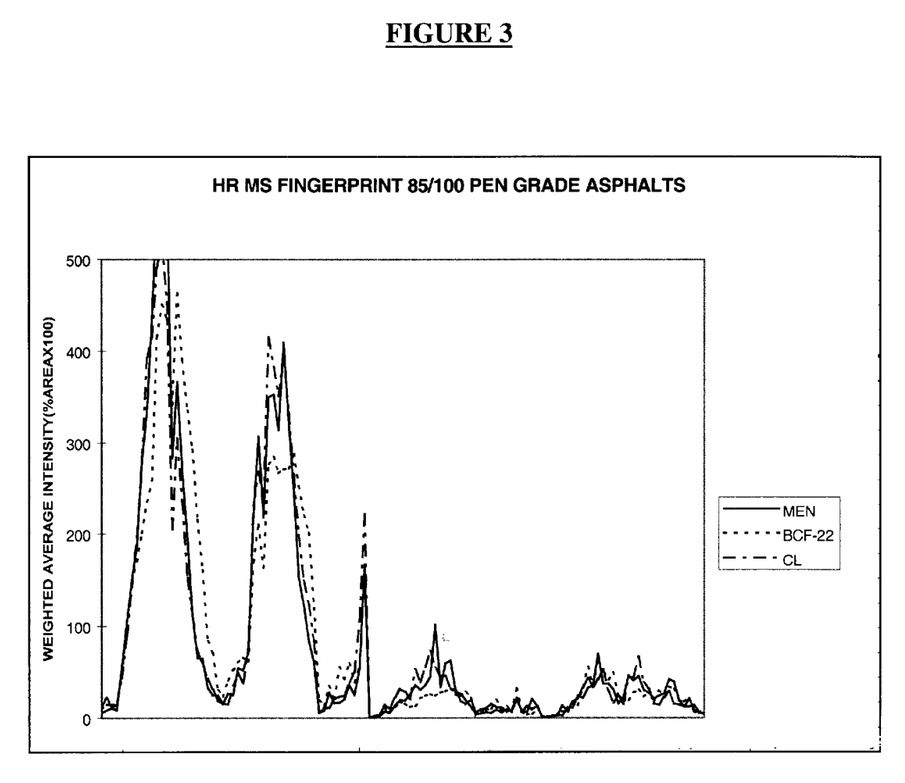
FIG. 3 shows a fingerprint spectra (intensity vs. mass) for asphalt from three representative crudes (MEN, BCF-22, and CL)

The molecular composition of asphalts in each group is consistent with the rheological performance using HR/MS fingerprint of 120 molecular groups of the formula $[C_nH_{(2n\pm z)}$—R]. FIG. 3 shows examples of how different crudes give asphalts with different compositions.

Mean intensities and standard deviations were calculated for Group I, II, III, and IV asphalts. A 95% confidence interval predicts the range for each molecular group in Group I, II, III, and IV asphalts. FIG. 1 shows representative data for groups I–IV.

TABLE 1

| PARAMETER | UNITS | COMMENTS |
| --- | --- | --- |
| CGSB Grade | A/B/C | Volatility, workability; A - excellent quality B - acceptable quality C - unacceptable quality |
| SUPERPAVE Spread | ° C. | Maximize spread |
| [Tmax-Tmin] Spread | ° C. | Maximize spread |
| Gg (Master curve @ 10° C.) | MPa | Maximum complex stiffness modulus of the material at glass transition (low temperature, impact loading). Maximize Gg |
| η0 (Master curve @ 10° C.) | MPa-s/rad | Theoretical complex viscosity at infinite loading time or high temperature, as a function of viscous-elastic transition. Maximize complex viscosity |
| ωc | rad/s | Viscous-elastic transition. |

TABLE 1-continued

| PARAMETER | UNITS | COMMENTS |
|---|---|---|
| | | Maximize frequency |
| R | N/A | Log ratio of Gg to Gωc, indicating the range of elastic response of the asphalt. Maximize R |
| [Tf-Tb] | ° C. | Temperature range for fully-viscous and fully-elastic phase response. Maximize [Tf-Tb] |
| [T45-Tb] | ° C. | Temperature range delineating fully-elastic phase response. Maximize [T45-Tb] |
| Penetration@ 25° C. | dmm | Given zero weighting in rheological ranking process. |
| SUPERPAVE PG | N/A | Given zero weighting in rheological ranking process |

HR/MS fingerprints using 120 molecular groups of the formula [$C_nH_{(2n\pm z)}$—R] are generated for vacuum residua from crude slate with unknown performance Twenty-four hydrocarbon molecular groups of the formula $C_nH_{(2n\pm Z)}$ are evaluated. Seventeen of the molecular groups (71% of the total) exhibit differences in intensity as a function of asphalt Theological ranking. Group I, II, III, and IV asphalts do not exhibit differences in intensity for low-aromaticity hydrocarbon molecular groups ($z \leq 8$). Group IV asphalts exhibit generally lower intensity for mid-aromaticity hydrocarbon molecular groups ($10 \leq z \leq 26$) than Group I, II, or III asphalts. Group IV asphalts exhibit generally higher intensities for high-aromaticity hydrocarbon molecular groups ($28 \leq z \leq 44$) than Group I, II, or III asphalts.

Nineteen molecular groups of the formula $C_nH_{(2n\pm z)}$—R where R is a single sulfur substitution, are evaluated for Group I, II, III, and IV asphalts. Ten of the molecular groups (53% of the total) exhibit differences in intensity between the four asphalt groups. Group I, II, III, and IV asphalts do not exhibit differences in intensity for low-aromaticity sulfur molecular groups ($z \leq 10$). Group III and Group IV asphalts exhibit generally lower intensities for mid-aromaticity sulfur molecular groups ($12 \leq z \leq 22$) than Group I and Group II asphalts. Group IV asphalts exhibit generally higher intensities for high-aromaticity sulfur molecular groups ($24 \leq z \leq 34$) than Group I, II, or III asphalts.

Ten molecular groups of the formula $C_nH_{(2n\pm z)}$—R where R=$S_2$, are evaluated for Group I, II, III, and IV asphalts. Three of the ten molecular groups (30% of the total) exhibit differences in intensity between the four asphalt groups. It is to be noted that the data exhibit high variability. In general, Group IV asphalts exhibit higher intensity for high-aromaticity $S_2$ molecular groups ($14 \leq x \leq 20$) than Group I, II, or III asphalts.

Twenty molecular groups of the formula $C_nH_{(2n\pm z)}$—R where R is a monatomic oxygen substitution, are evaluated for Group I, II, III, and IV asphalts. Twelve of the twenty molecular groups (60% of the total) exhibit differences in intensity between the four asphalt groups. As with the disulfide molecular groups, the oxygen molecular groups exhibit high variability in intensity within each asphalt group. Group I, II, III, and IV asphalts do not exhibit differences in intensity for low-aromaticity oxygen molecular groups ($z \leq 10$). Group IV asphalts exhibit lower intensities for mid-aromaticity oxygen molecular groups ($12 \leq z \leq 20$) than Group I, II, and III asphalts. Group III and IV asphalts exhibit lower intensities for high-aromaticity oxygen molecular groups ($22 \leq z \leq 32$) than Group I, or II asphalts. For molecular groups where $z \leq 32$, there are no differences in intensity between the four asphalt groups.

Fourteen molecular groups of the formula $C_nH_{(2n\pm z)}$—R where R=$O_2$, are evaluated for Group I, II, III, and IV asphalts. Twelve of the twenty molecular groups (85.7%) exhibit differences in intensity between the four asphalt groups. As with the $S_2$ and monatomic oxygen molecular groups, the $O_2$ molecular groups exhibit high variability in intensity within each asphalt group. For $O_2$ molecular groups where ($4 \leq x \leq 22$), Group I, II, and III asphalts exhibit higher intensities than Group IV asphalts.

Seventeen molecular groups of the formula $C_nH_{(2n\pm z)}$—R where R is a monatomic nitrogen substitution, are evaluated for Group I, II, III, and IV asphalts. There is no trend between intensity of nitrogen molecular groups and rheological performance of the four asphalt groups.

Five highly aromatic molecular groups of the formula $C_nH_{(2n\pm z)}$—R where R=SO are evaluated. All five groups (100%) exhibit intensity effects as a function of rheological performance ranking. Group I, II, and III asphalts exhibit higher intensities for $C_nH_{(2n\pm z)}$—R where R=SO and ($16 \leq z \leq 20$). Group III and IV asphalts exhibit lower intensities where ($22 \leq z \leq 26$) than Group I, and II asphalts.

Five molecular groups of the formula $C_nH_{(2n\pm z)}$—R where R=NO are evaluated for Group I, II, III, and IV asphalts. All five molecular groups (100%) exhibit differences in intensity between the four asphalt groups. Group I, II, and III asphalts exhibit higher intensity for NO molecular groups ($9 \leq z \leq 21$) than Group IV asphalts.

Miscellaneous molecular groups of the formula $C_nH_{(2n\pm z)}$—R where R=$O_3$, $SO_2$ or $NO_2$ are evaluated for Group I, II, III, and IV asphalts. Group I, II, III, and IV asphalts do not exhibit differences in intensity for $O_3$ or $NO_2$ molecular groups. Group I, and II asphalts exhibit slightly higher intensity for $SO_2$ molecular groups than Group III and IV asphalts.

HR/MS fingerprints were generated for 31 vacuum residua from eleven different crude slates. Rheological indices and rheological parameters were available for a subset of 27 residua from ten crude slates shown in FIG. 4. (MEN=Menemoto; BCF-22=Bachequero-22; CL Cold lake; BR=Bow River; AHF=Arabian Heavy/Forties blend)

The overall ordinal ranking for each crude slate was determined by taking the mean ordinal ranking for each vacuum residua from that crude slate and calculating the mean value of the means.

The molecular composition of asphalts in each group was examined to determine if there were differences between the four groups which were consistent with the differences in rheological performance using HR/MS fingerprint of 120 molecular groups of the formula [$C_nH_{(2n\pm x)}$—R]. Mean intensities and standard deviations were calculated for Group I, II, III, and IV asphalt. A 95% confidence interval was used to predict the range of intensity for each molecular group in Group I, II, III, and IV asphalts.

Based on mean values of intensity, aromaticity, carbon number and molecular weight for each rheological group, Molecular profiles were plotted for the following functional relationships using a library of at least 120 molecular groups:

(a) intensity=f(molecular group, aromaticity)
(b) aromaticity=f(molecular group, intensity)
(c) mean alkyl side chain length=f(molecular group, aromaticity)
(d) mean molecular weight=f(molecular group, aromaticity)

Comparison of molecular profiles delineated statistically significant differences in molecular composition between good (Group I) and poor (Groups IV and V) asphalts which formed the basis for the optimal asphalt composition definitions. The molecular moment (first moment of area under the curve) is calculated for each of the functional relationships above:

(a) Ri=the intensity moment for molecular group R
(b) Rz=the aromaticity moment for molecular group R
(c) Rc=the mean alkyl side chain length moment for molecular group R
(d) Rm=the mean molecular weight for molecular group R The differences in the HR/MS fingerprints of Group I and Group IV asphalt are illustrated in FIG. 1. Asphalts can be ranked for relative field performance based on their parent crude oil or crude oil blend. The rheological ranking system is based on a combination of performance parameters from empirical and mechanistic asphalt binder tests which accurately reflect and predict the performance of pavements incorporating the asphalt. Different asphalt groups (i.e. Groups I, II, III, and IV) identified by the rheological ranking system exhibit different molecular compositions. The molecular composition of asphalts in a rheological group is similar. The differences in molecular composition between asphalt groups are consistent. The rheological performance and the field performance of an asphalt can be predicted by its molecular composition.

The Theological performance and the pavement performance of an asphalt can be optimized by selecting asphalts and parent crudes or crude blends that maximize the concentration of components with beneficial properties, and that minimize the concentration of components with detrimental, or other non-beneficial properties.

Typical heavy crudes employed in asphalt manufacture, such as Menemoto (MEN), Boundary Lake (BL) and Cold Lake (CL) asphalts/vacuum residua with penetrations in the 85/100 range were selected for preliminary fingerprinting. The three asphalts exhibit distinctly different pavement performances. Initial HR/MS fingerprints were generated for the polar-1 fractions. Sulfoxides, carboxylic acids, phenols, and pyridines were identified in SHRP A341 document as the polar functional groups primarily responsible for adhesion to aggregates.

Figure 2:
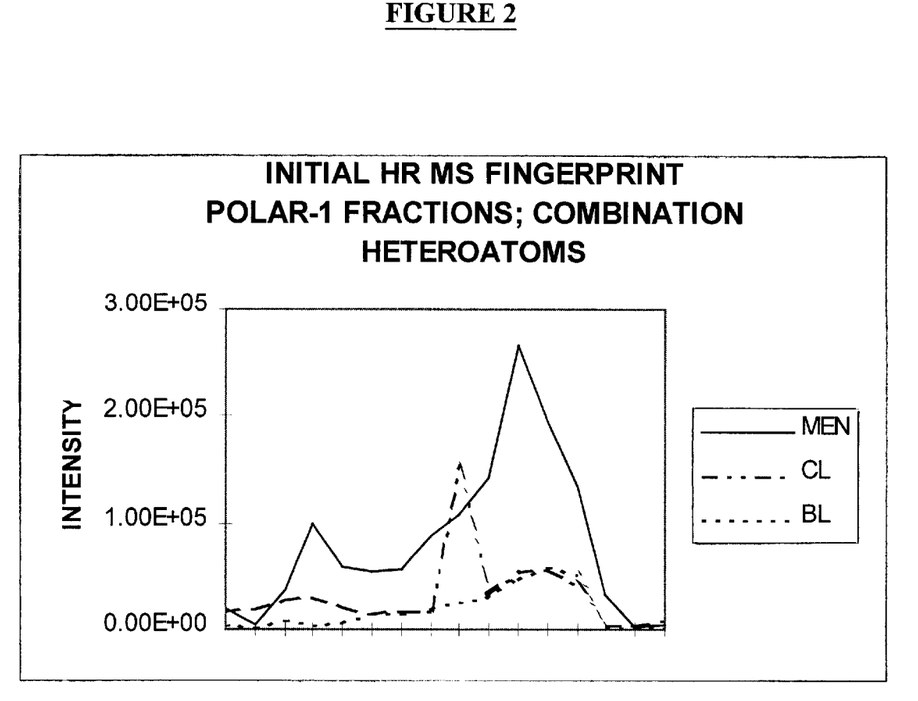
FIG. 2 shows fingerprint spectra (intensity vs. mass) for fractions from three representative crudes (MEN, CL, and BL)

The HR/MS fingerprints are shown in FIG. 2 for fractions from three representative crudes. Data were analyzed for statistical significance using Excel 5.0 Two Factor Analysis of Variance (ANOVA) without Replication at a 0.05 Level of Significance. Analysis indicated that the HR/MS fingerprinting technique could differentiate between the three asphalts based on combination heteroatom fragments at a 0.05 Level of Significance. The MEN residuum exhibited higher intensity than the other two asphalts for each molecular species evaluated, indicating a more polar material. The CL and BL asphalts were differentiated by differences in sulfite intensity.

The preliminary results demonstrated that asphalts can be fingerprinted and that asphalts of different quality exhibit different concentrations of molecular fragments. The significance of a particular fragment or its contribution to asphalt performance was not determined.

The second generation HR/MS fingerprints was based on an expanded materials library of combination heteroatoms and included both aromatic and polar-1 fractions, effectively increasing the proportion of asphalt evaluated to greater than 50 weight percent. Normalized molecular fragment distributions were used to construct the second generation HR/MS fingerprints. The fingerprints of all asphalts/residua belonging to a single penetration grade or SUPERPAVE™ PG grade were evaluated to determine which functional groups generated statistically-unique fingerprints.

The HR/MS fingerprints for a typical 85/100 penetration asphalts from three different crudes like Menemota (MEN), Bachequero-22 (BCF-22) and Cold Lake (CL) is shown in FIG. 3.The data were examined using Excel 5.0 to ensure that there was a statistically-significant difference between asphalts from different crude sources. There was no statistically-significant difference between different source asphalts using the entire library of molecular species. There was no statistically-significant difference using the combination heteroatom subset which had proven successful in the first generation fingerprints. When a subset of oxygen, nitrogen, and combination heteroatom groups were used, the softer asphalts exhibited a statistically-significant difference and the 85/100 penetration (SUPERPAVE PG 58-22) asphalts exhibited differences which were borderline. HR/MS fingerprints which incorporate oxygen, nitrogen, and combination heteroatom functional groups can be used to develop improved compositional indices. FIG. 4 shows the effect of compositional changes in the crude on mass specta.

Residuum samples for HR/MS are preferably prepared using an apparatus which can accurately heat the whole crude at a selected temperature for a given period of time at constant low pressure. It is important that the apparatus demonstrates excellent long-term stability for both temperature and vacuum conditions. The temperature and vacuum of the apparatus may be variable although once the temperature corresponding to the target atmospheric equivalent temperature (AET) at a given pressure has been established, then both temperature and pressure are maintained constant throughout the experiment. Incorporation of sub-ambient (vacuum) pressure in the experiment prevents thermal cracking of the asphalt/residuum. To obtain the asphalt/residuum, it is necessary to determine the exact temperature-pressure combination which corresponds to the target AET. This can be done as outlined in ASTM D5236; however that procedure requires accurate measurement of both temperature and pressure. It is simple to measure the temperature of the apparatus during this procedure however it is generally difficult to measure the working pressure. To avoid direct measurement of pressure, this method uses the distillation profiles of a set of known crudes to calibrate the apparatus for temperature-pressure conditions. Correlation of process temperature readout to AET is determined using the calibrant crudes distillation profiles.

The preferred method is to place a weighed, frozen crude sample in a small closed chamber, that is then roughly pumped down by a mechanical pump, and then opening a passage from the small closed chamber to a chamber with at least 1 L volume (i.e., heated manifold) at a know vacuum level (e.g., 1 milliTorr). Intermediate products, resids, and aged asphalt can be used instead of or mixed with the crude. Preferred samples sizes are 10–40 mg, though 2–200 mg are envisioned as part of this invention. The resid remaining after equilibrium is then taken out and reweighed. The ratio of the first weighing to the second weighing gives the AET yield. Other information can be determined from analyzing gases from the vacuum pump line or the vacuum chamber depending on whether the vacuum chamber is continuously pumped down or closed off after reaching the required pressure and then exposed to the sample.

The preferred apparatus has a sample oven, a sample holder, and an all-glass heated manifold. The apparatus is capable of achieving 1 milliTorr ($10^{-3}$ Torr) absolute pressure. The sample is weighed into a quartz tube boat and cooled in a liquid nitrogen bath. It is then placed in sample holder and attached to manifold. High temperature glass valves in the manifold are used to expose the sample to sub-ambient pressure. Other boats may be used, though quartz is preferred. On exposure of the sample to vacuum pressure, the sample oven is heated from ambient to target temperature and maintained at that temperature for a selected time period. The manifold, which is maintained at constant high temperature (300–350° C.) throughout sample preparation, permits a physical interface between the sample holder and the vacuum pressure generated by the apparatus. In this manner, it is not necessary to develop and disperse vacuum pressure for each crude to be reduced. This greatly decreases sample preparation time for asphalt/residuum from whole crude.

Approximately 20 g of asphalt or residuum is produced from 5 ml of whole crude by this method, depending on AEBP and the nature of the crude. Preferred sample formats are sheets, thin films, and drops. These sample forms allow for a high enough surface area to rapidly cool or heat the sample. A higher vacuum (lower pressure) in the oven allows a lower oven temperature and therefore less sample degradation. The preferred mode of this invention uses fixed temperature ovens with sample equilibration time of less than or equal to 15 minutes, a constant vacuum buffer, and a 0.2% repeatability. The term "freezing" means cooling to a temperature low enough such that water does not vaporize enough in at least 30–60 seconds to cause sample damage.

What is claimed is:

1. A method for selecting crude or crude residuum as a source for asphalt, comprising a) determining an optimal asphalt composition from molecular moments by:
   selecting the crude or the crude residuum;
   producing an asphalt out of the crude or crude residuum;
   performing a rheological test on a sample of the asphalt to determine the rheological index of the sample;
   determining a mean rheological index of the crude slate by repeating the rheological test and averaging the rheological index;
   assigning a rheological group to the mean rheological index;
   calculating a mean intensity, an aromaticity, a carbon number, and a molecular weight for each of the rheological groups;
   calculating each the molecular moments as=SUM (intensity×aromaticity)/SUM(aromaticity);
   comparing the molecular profiles of the rheological groups of good and poor asphalts; and
   confirming the statistical significance of the differences using the molecular moments;
b) then predicting asphalt performance of the crude or crude residuum from molecular composition by
   selecting the crude or crude residuum;
   performing high resolution mass spectrometry on a sample to determine a plurality of molecular groups;
   calculating mean values for each molecular group;
   determining a predicted theological index of the sample;
   comparing the predicted rheological index to the rheological index of good and poor asphalts;
   determining the rheological group of the sample;
   predicting the suitability of the crude slate for asphalt manufacture based on the rheological group; and
   confirming the suitability of the crude slate for asphalt manufacture by comparison with the rheological group of good and bad asphalts.

2. A method according to claim 1, wherein the rheological index is calculated from the formula 13.8639−1.18964 E-1*Hc+6.12843 E-2 Hi−4.10153 E-1 Hz−4.68191 E-3 Ni+6.65557 E-3 Oi+5.88057 E-3 Sm−1.42995 E-1 Sz−3.14998 E-3 [C5ARings−]−3.35754 E-3 [C5ARings+] wherein $R^2=0.95$.

3. A method according to claim 1, wherein the mean values are obtained by multiple linear regression, principal components regression, partial least squares regression, or constrained principal spectra analysis.

4. A method according to claim 1, wherein the crude is blended.

5. A method according to claim 1, wherein the crude residuum is prepared by:
   cooling a sample of the crude to an average temperature of about −200 to 0° C.;
   placing the cooled sample in a chamber,
   wherein the chamber has a absolute pressure within the range of about $10^{-3}$ to $10^{-6}$ Torr and
   a fixed temperature within the range of about 340 to 540° C.,
   such that the combination of the absolute pressure and the fixed temperature is equivalent to an atmospheric equivalent boiling point for the residuum to be produced,
   such that the sample is so small or so thin so as to reach equilibrium with the temperature in the chamber within 15 minutes; and
   keeping the sample in the chamber at the absolute pressure and the fixed temperature for 5 to 60 minutes until essentially only the residuum remains from the sample.

6. A method according to claim 1 wherein the asphalt is first produced as a residuum specimen from a crude, by a method comprising:
   cooling a sample of the crude to an average temperature of about −200 to 0° C.;
   placing the cooled sample in a chamber,
   wherein the chamber has a absolute pressure within the range of about $10^{-3}$ to $10^{-6}$ Torr and
   a fixed temperature within the range of about 340 to 540° C.,
   such that the combination of the absolute pressure and the fixed temperature is equivalent to an atmospheric equivalent boiling point for the residuum to be produced,
   such that the sample is so small or so thin so as to reach equilibrium with the temperature in the chamber within 15 minutes; and
   keeping the sample in the chamber at the absolute pressure and the fixed temperature for 5 to 60 minutes until essentially only the residuum remains from the sample.

7. A method according to claim 1, wherein the rheological test measures at least one of isochrones, master curves and black diagrams to represent viscoelastic behavior.

8. A method according to claim 1, wherein the rheological test measures at least one member selected from the group consisting of viscosity @ 135° C., SUPERPAVE PG temperature spread, [Tmax−Tmin], and penetration @ 25° C.

9. A method to predict the potential quality of asphalt from crude oils or blends of crude oils of various origins by calculating their molecular moments of intensity, aromaticity, alkyl side chain length and molecular weight using detailed molecular composition and structure data from high resolution mass spectrometry, using a molecular library of at least 100 molecular species of the formula $[C_nH_{(2n\pm z)}-R]$ where "n" may equal 0 but is generally greater than ten; "z" ranges from approximately −4 to +44;

and "R" is a heteroatom or combination of heteroatoms which usually but not always contains sulfur, nitrogen, or oxygen or a combination of these, or other heteroatoms, relating molecular moments to a comprehensive performance parameter which encompasses rheological performance measurements, relating the comprehensive performance parameter to actual pavement performance of asphalts manufactured from crude oils or crude oil blends.

10. A method according to claim 9 wherein a sample is generated for this method by sampling asphalt, separating fractions of asphalt samples based on solubility class or functionality or molecular size or polarity or other separation techniques, producing crude oil residua by conventional or non-conventional distillation or whole crude reduction techniques; all of which may be performed on crude oil or crude oil blends with known or unknown components and proportions.

11. A method according to claim 9 wherein the comprehensive performance parameter may be calculated by mathematically combining at least one member selected from the group consisting of conventional asphalt properties measures at least one member selected from the group consisting of viscosity @ 135° C., SUPERPAVE PG temperature spread, [Tmax−Tmin], and penetration @ 25° C.

12. A method according to claim 9 wherein the validity of the comprehensive performance parameter is tested by calculating the mean value of the comprehensive performance parameter from the individual values of the comprehensive performance parameter for all samples belonging to one crude slate, ranking the crude slate according to mean value of the comprehensive performance parameter against other crude slates, and comparing the crude ranking based on mean performance to the field performance of asphalt pavements which incorporate that crude or crude blend.

13. A method according to claim 9, wherein crude slates are selected based on maximizing a majority of the mass intensities for a molecular structure represented by $C_nH_{(2n\pm z)}$—R wherein hydrocarbon molecular groups $10 \leq z \leq 26$, sulfur molecular groups $12 \leq z \leq 22$, monoatomic oxygen molecular groups $12 \leq z \leq 20$ and for high-aromaticity oxygen molecular groups $22 \leq z \leq 32$ high-aromaticity $S_2$ molecular groups $14 \leq x \leq 20$ diatomic oxygen molecular groups $4 \leq z \leq 22$ SO molecular groups $16 \leq z \leq 26$, NO molecular groups $9 \leq z \leq 21$ $SO_2$ molecular groups;

and minimizing a majority of the mass intensities for hydrocarbon molecular groups $28 \leq z \leq 44$, high-aromaticity sulfur molecular groups $24 \leq z \leq 34$; and not differentiating for molecular groups where $z > 32$.

* * * * *